(12) United States Patent
Rieder

(10) Patent No.: US 6,330,064 B1
(45) Date of Patent: Dec. 11, 2001

(54) DOUBLY-DIFFERENTIAL INTERFEROMETER AND METHOD FOR EVANESCENT WAVE SURFACE DETECTION

(75) Inventor: Ronald J. Rieder, Medford, MA (US)

(73) Assignee: SatCon Technology Corporation, Cambridge, MA (US)

( * ) Notice: Subject to any disclaimer, the term of this patent is extended or adjusted under 35 U.S.C. 154(b) by 0 days.

(21) Appl. No.: 09/780,792

(22) Filed: Feb. 9, 2001

Related U.S. Application Data

(60) Provisional application No. 60/188,808, filed on Mar. 13, 2000.

(51) Int. Cl.$^7$ ....................................................... G01B 9/02
(52) U.S. Cl. ................................................................. 356/481
(58) Field of Search ................................... 356/477, 481; 385/12, 14; 250/227.14, 227.19, 227.27

(56) References Cited

U.S. PATENT DOCUMENTS

| | | | |
|---|---|---|---|
| 4,640,615 | * 2/1987 | Sasaki | 356/481 |
| 4,940,328 | 7/1990 | Hartman | 356/481 |
| 5,081,012 | * 1/1992 | Flanagan et al. | 356/73.1 |
| 5,120,131 | 6/1992 | Lukosz | 356/481 |
| 5,335,065 | * 8/1994 | Lequime et al. | 356/453 |
| 5,465,151 | 11/1995 | Wybourne et al. | 356/481 |
| 5,623,561 | 4/1997 | Hartman | 385/12 |

OTHER PUBLICATIONS

W. Lukosz, et al., *Elsevier Science S.A.*, Difference interferometer with new phase–measurement method as integrated–optical refractometer, humidity sensor and biosensor, pp. 316–323 (1997).

W. Lukosz, *Elsevier Science S.A.*, Integrated optical chemical and direct biochemical sensors, pp. 37–50 (1995).

C. Stamm, et al. *Elsevier Science S.A.*, Integrated optical difference interferometer as immunosensor, pp. 203–207 (1996).

B. J. Luff, et al., *Journal of Lightwave Technology* vol. 16, No. 4 (Apr. 1998) Integrated Optical Mach–Zehnder Biosensor, pp. 583–592.

H. Helmers, et al., *Applied Optics* vol. 35, No. 4, (Feb. 1, 1996) Performance of a compact, hybrid optical evanescent–wave sensor for chemical and biological applications, pp. 676–680.

* cited by examiner

*Primary Examiner*—Samuel A. Turner
(74) *Attorney, Agent, or Firm*—Dike, Bronstein, Roberts & Cushman—IP Group; George W. Neuner; George W. Hartnell, III

(57) ABSTRACT

A high speed, highly sensitive optical sensing platform and a method for detecting and/or measuring characteristics of a substance in a measurement sample are disclosed. The platform includes at least one pair of optical paths formed in a waveguide, a light source for injecting optical beams along the optical paths, a light modulator for enabling the excitement of a transverse electric and a transverse magnetic guide modes, and a phase detector for detecting phase differences between the beams propagating along the optical paths. One of the optical paths has a target analyte of unknown concentration with a measurement sample bound to its upper surface, while the second optical path has a reference sample containing a known concentration of the target analyte bound to its upper surface. A guided mode modulator causes an optical beam to propagate through the waveguide sequentially as two polarized modes. The highly sensitive platform is especially useful for directly detecting and/or measuring very small numbers of small molecules, bio-molecules, microorganisms in a liquid or gaseous test sample.

38 Claims, 3 Drawing Sheets

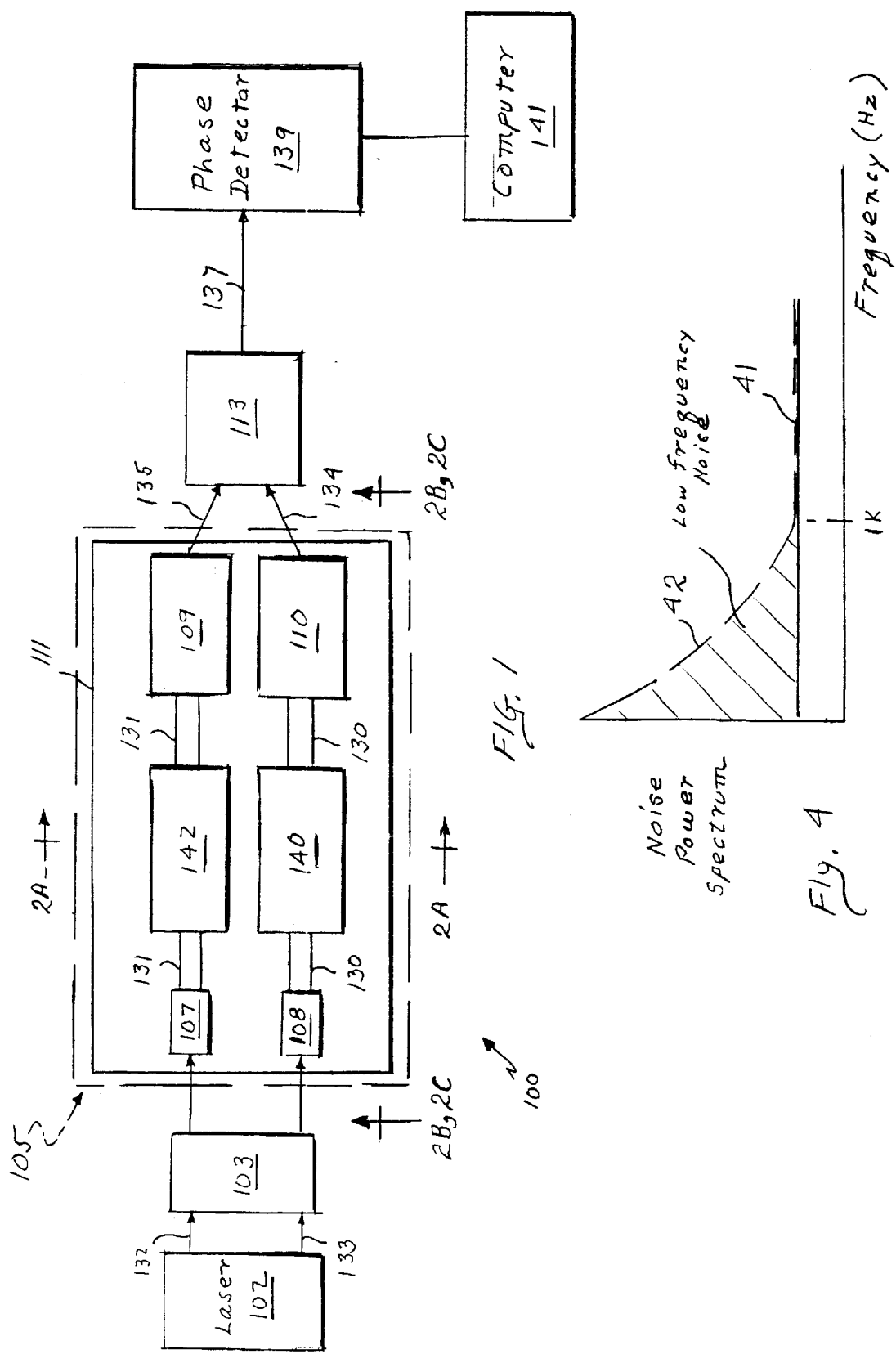

DOUBLY-DIFFERENTIAL INTERFEROMETER AND METHOD FOR EVANESCENT WAVE SURFACE DETECTION

CROSS REFERENCE OR RELATED APPLICATIONS

This application claims the benefit of U.S. Provisional Application No. 60/188,808 filed Mar. 13, 2000.

BACKGROUND OF THE INVENTION

1. Field of the Invention

This invention relates generally to optical sensors, and more particularly to high speed, highly sensitive, optical sensing platforms for evanescent wave surface detection applications, i.e., an evanescent interferometer biosensor.

2. Discussion of Related Art

Evanescent wave surface detection is an optical technique that has been used in various applications such as the detection of substances in liquid and gaseous samples and the measurement of certain properties of liquid and gaseous samples, including, e.g., changes in refractive indices and ionic concentrations of the samples.

The evanescent wave surface detection technique typically includes sensing a change in the local environment at the surface of a waveguide. The waveguide surface is often coated with a chemically or biologically sensitive layer, to which targets within a liquid or gaseous sample are then bound. Light is coupled into the waveguide, which, as it propagates through the waveguide, produces evanescent wave fields that reach out and penetrate the chemically or biologically sensitive layer and the sample bound thereto. Because evanescent wave fields that correspond to different spatial modes of the propagated light typically penetrate at different depths, information relating to the depths of penetration for the different spatial modes can be used to characterize the liquid or gaseous sample provided at the surface of the waveguide.

For example, the detection and/or measurement of very small numbers of microorganisms in a sample, using evanescent wave surface detection techniques, typically requires amplification, or enrichment, of the target microorganisms population before detecting and/or measuring the sample is possible. This is often accomplished using culture enrichment techniques that may take up to several days to complete. However, some evanescent wave surface detection techniques permit direct and rapid detection and/or measurement of very small numbers of target microorganisms by transferring the amplification process from the biological domain to the photonic domain.

One such evanescent wave surface detection technique uses fluorescent markers for detecting and/or measuring substances in a liquid or gaseous sample. Specifically, targets, i.e., analytes, within a sample, which are bound to the surface of a waveguide, are tagged, or labeled, with fluorescent markers. Light is coupled into the waveguide. As the light propagates through the waveguide, evanescent wave fields reach out into the tagged sample and excite the fluorescent markers. The target microorganisms in the tagged sample are then detected and/or measured by monitoring the intensity of the sample's fluorescence.

An evanescent wave surface detection technique that uses fluorescent markers, however, has some shortcomings. For example, the expense and complexity of reagents used for tagging the targets affect its utility. Still further, the process of tagging the sample with fluorescent markers has some drawbacks. Specifically, it is often difficult to ensure that only the target analytes are tagged. Frequently, however, random substances bound to the waveguide surface are tagged also, thereby affecting the detection and/or measurement of the desired targets. Such non-specific binding of random substances can adversely affect, e.g., the signal-to-noise ratio (SNR) of that evanescent wave surface detection technique.

Another optical evanescent wave surface detection technique that can be used to detect and/or measure small numbers of target analytes within a sample involves monitoring changes in the intensity of light related to the evanescent wave fields due to the bound sample. This evanescent wave surface detection technique is used in some commercially available instruments, such as the BIAcore™ surface plasmon resonance (SPR) instrument manufactured by Amersham Pharmacia Biotech AB, Uppsala, Sweden.

Specifically, the evanescent wave surface detection method used with an SPR instrument typically comprises coating the waveguide surface with a thin layer of metal; immobilizing "selective" receptors to the metal layer; and then capturing the sample onto the receptors. Light is coupled into the waveguide, which, as it propagates through the waveguide, causes evanescent wave fields to reach out into the sample layers on the waveguide surface. The bound targets alter the effective index of refraction (n) of the metal layer. The evanescent wave fields resonantly transfer energy to a surface plasmon, and the intensity of the evanescent wave fields is monitored at an energy matching condition.

However, an evanescent wave surface detection technique used with the SPR instrument has some shortcomings. For example, biochemical and environmental factors such as non-specific binding and temperature variation typically limit the sensitivity and stability of that evanescent wave surface detection technique. Furthermore, the BIAcore™ brand SPR instrument is commercially expensive; hence, it is often inappropriate for use in low-cost applications.

Still another evanescent wave surface detection technique for detecting and/or measuring untagged substances in a bound sample is disclosed in U.S. Pat. No. 5,120,131 (the "'131 patent") to Lukosz. According to that disclosed invention, a measurement sample is bound to the waveguide surface, and light is coupled into the waveguide, thereby causing evanescent wave fields to reach out into the bound sample. Specifically, light is coupled into the waveguide so that two mutually coherent, orthogonally polarized modes propagate through the waveguide simultaneously and coaxially. As a result of the interaction between the propagated light and the bound sample, the respective refractive indices of the two guided modes, i.e., the transverse electric (TE) and transverse magnetic (TM) change. Relative changes in the refractive index (n) of a measurement sample with respect to the refraction index of a reference sample can be measured with an interferometer, and those measurements can be used for characterizing the bound sample. These changes are manifest as an optical phase change of light traveling through a medium.

However, the evanescent wave surface detection technique disclosed in the '131 patent has some shortcomings. For example, this evanescent wave surface detection technique typically lacks the stability required for accurately detecting and/or measuring very small numbers of targets. This is because the stability of that evanescent wave surface detection technique typically is limited by biochemical and environmental factors, i.e., noise, such as non-specific binding and temperature variation of the bulk liquid, which often result in less than optimal SNR ("signal-to-noise ratio"). Moreover, thermal and mechanical perturbations, which are major sources of noise and which adversely affect the SNR.

It would be desirable, therefore, to provide an improved evanescent wave surface detection technique and device for detecting and/or measuring substances in liquid and gaseous samples. Such an evanescent wave surface detection technique and device would have the stability and sensitivity required for accurately and directly detecting and/or measuring low levels, e.g., as low as a single microorganism, of small molecules, bio-molecules, and/or microorganisms in a sample. Moreover, such a detection technique would have the stability and sensitivity required for accurately and directly detecting and/or measuring low levels of small microorganisms without requiring prior amplification, i.e., enrichment, of the target analyte population. It would also be desirable to have an evanescent wave surface detection technique and device for detecting and/or measuring small numbers of small molecules, biomolecules, and/or microorganisms in a sample that provides results quickly and can be implemented at relatively low cost. Furthermore, it would be desirable to have an evanescent wave surface detection technique and device that removes noise associated with thermal and mechanical perturbations to maximize the SNR.

SUMMARY OF THE INVENTION

The present invention provides a high precision, optical sensing platform that uses a waveguide, which includes at least one first optical path in relatively close spatial proximity to at least one second optical path. The first optical path are exposed to measurement samples containing targets, which are bound to a surface contiguous to the first optical path of the waveguide. The second optical path can be exposed to reference samples, which have known targets bound to a surface contiguous to the second optical path of the waveguide. The measurement and reference samples containing the targets can be either liquid or gaseous samples.

In a preferred embodiment, light enters a polarization modulator, which facilitates removing low frequency noise signals. The polarization modulator enables exciting two orthogonally polarized spatial, i.e., guided, modes, causing each guided mode to propagate independently and sequentially through the spatially separated measurement and reference optical paths. Subsequently, the light from each path can be coupled out of the waveguide and coherently combined for each polarization mode. An optical phase detector can be used to record any changes in phase for each guided mode and to compare any changes with subsequent measurements. These optical phase changes, typically, are caused by characteristics of the measurement and reference samples and the targets bound thereto, which samples are contiguous to the surface of the waveguide.

According to a preferred embodiment of the present invention, optical phase changes caused by the characteristics of the target analytes bound to measurement and reference samples can be detected and/or measured using a doubly differential surface detection technique, which comprises a set of first differential measurements and a second differential measurement. Specifically, a set of first differential measurements is obtained from any optical phase change between the reference and measurement samples for each of the individual orthogonal guided modes, each of which propagates sequentially through the first and the second optical paths of the waveguide. A second differential measurement is obtained from a combination of the first differential measurements of optical phase changes for each of the individual guided modes.

More specifically, the set of first differential measurements is obtained by first determining changes in the respective effective refractive indices ($\delta n$) between the first and second optical paths, which are exposed to a measurement sample and a reference sample, respectively. This "set" of measurements comprises an effective refraction index change for each of the two polarized guided modes, i.e., $\delta n_{TE}$ and $\delta n_{TM}$, which, because of modulation, propagates through each of the optical paths sequentially rather than simultaneously. Further, the second differential measurement is obtained by determining an overall change in the effective refractive indices ($\Delta N$) between the respective polarized guided modes, i.e., $\Delta N = \delta n_{TE} - \delta n_{TM}$. Changes in the effective refractive indices of the first and second optical paths are caused by (a) the characteristics of the target analytes bound to the measurement and reference surfaces of the waveguide and also (b) by the polarized guided mode propagating through the waveguide.

Advantageously, this doubly differential surface detection technique, as implemented on the optical sensing platform of the present invention, provides immunity to environmental effects, such as temperature changes, mechanical vibrations, and biochemical effects, such as non-specific binding, thereby providing the sensitivity and speed required for directly detecting and/or measuring, in real time, very small numbers of bound targets, e.g., small molecules, bio-molecules, and/or microorganisms, including a single target, bound to or contained within the sample.

Because change in refractive index ($\delta n$) is dependent on the polarization of the light, the optical response of the polarized light is different for each of the orthogonally guided modes that propagate within the waveguide. Modulating the polarization of the incident light enables exciting two guided modes at modulation frequencies above that of a predetermined unwanted noise distribution. Moreover, subtracting temporally adjacent measurements in the reference and measurement samples results in the common-mode rejection of in-band noise. Thus, noise due to thermal and mechanical perturbations, which is generally restricted to temporal frequencies similar to those of the target signal (less than about a few thousand Hertz) is substantially eliminated, significantly improving the SNR.

Still further aspects and advantages of the present invention will become apparent from a consideration of the ensuing description and drawings.

BRIEF DESCRIPTION OF THE DRAWINGS

The invention will be better understood by reference to the following more detailed description and accompanying drawings, wherein like elements correspond to like elements, in which:

FIG. 1 illustrates a block diagram of an embodiment of an optical sensing platform according to the present invention;

FIG. 4 shows the dramatic effect of polarization modulation on power spectral density.

Figure 2A:
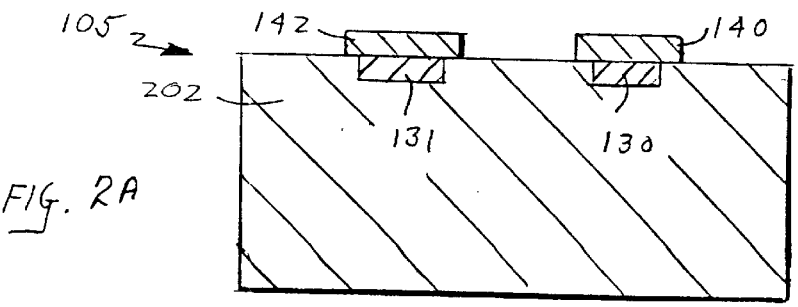
FIG. 2A illustrates a cross sectional view of an embodiment of an integrated optical sensor used with the optical sensing platform of FIG. 1, taken along a line 2A—2A.

DETAILED DESCRIPTION OF THE INVENTION INCLUDING THE PREFERRED EMBODIMENTS THEREOF

As shown in FIG. 1, an optical sensing platform 100 in accordance with one embodiment in the present invention includes a light source, e.g., laser 102, a polarization modulator 103, an integrated optical sensor 105, a beam combiner 113, a phase detector 139, and a computer 141.

The light source, e.g., laser 102, injects beams 132, 133 into a polarization modulator 103. The polarization modulator 103 rotates, or modulates, the polarization of the incident light to enable the excitement of two orthogonally polarized guided modes, e.g., the $TE_m$ (transverse electric) and $TM_m$ (transverse magnetic) modes, in each of the measurement and reference paths 130, 131. Moreover, the polarization modulator 103 causes the two polarized guided modes to propagate sequentially through both the measurement and reference paths 130, 131. The polarization modulator 103 can be of any type that is well known to those of ordinary skill in the art, e.g., a ferro-electric liquid crystal, pockel cell or photoelastic modulator, that switches between S and P polarization to excite the transverse electric and the transverse magnetic guided modes in time, removing low frequency noise and eliminating long-term drift.

Modulating the polarization of the incident beams 132, 133, alternately exciting the $TE_m$ and $TM_m$ guided modes at modulation frequencies above that of a predetermined unwanted noise distribution and subtracting adjacent measurements, e.g., from the reference sample 142, results in the common-mode rejection of the low frequency noise sources. Major sources of noise limiting the performance of interferometric systems typically are due to thermal and mechanical perturbations. These noise sources are generally confined to temporal frequencies well under a thousand Hertz. Thus, obtaining the desired information from a differential measurement and employing active common-mode rejection techniques significantly suppresses these external disturbances to increase the system signal-to-noise ratio (SNR). The advantage of this method is the ability to suppress unwanted signals within the bandwidth of the desired information. Conventional low-pass filtering is used to suppress unwanted signals outside of the bandwidth of the desired signal. However, with low-pass filtering, any noise occurring within the signal bandwidth cannot be suppressed without also suppressing the desired signal.

The dramatic effect of polarization modulation is shown in FIG. 4, which shows the noise power spectrum for a typical interferometric system. Without modulation, the curve 42 (shown in FIG. 4 as a dashed line) exhibits significantly higher noise power at low frequencies, typically below about 1000 Hertz. With polarization modulation, however, the curve 41 (shown in FIG. 4 as a straight line) is virtually constant at all frequencies, including in-band frequencies, i.e., frequencies within a desirable bandwidth. Indeed, polarization modulation filters out low-frequency noise (shown in FIG. 4 as the hatched region), typically due to thermal and mechanical perturbations, as would a low-pass filter if applied to the entire spectrum.

This common-mode rejection technique is readily applied to an interferometric evanescent wave biosensor. In such a device the response to the surface binding of select, e.g., biochemical molecules, is manifest as a change in the effective refractive index within the guiding region of a single-mode waveguide 111. This index change is dependent on the polarization of the light. Moreover, the optical response for S- and P- polarized light (respectively propagated as TE and TM spatial modes within a waveguide 111) is different, however, many externally applied perturbations are independent of polarization. By modulating the polarization of the incident light at a rate at least two times the signal bandwidth to excite alternatively the TE and TM guided modes and subtracting corresponding values of $\phi_{TE}$ and $\phi_{TM}$ in time, where $\phi$ is the optical phase, in-band perturbations common to both $\phi_{TE}$ and $\phi_{TM}$ is removed leaving only the desired signal and thus a robust system.

The modulated light then passes into input couplers 107, 108 of a waveguide 111, which causes respective, in-coupled, guided beams (not shown) to propagate, respectively, through the optical paths 131, 130 toward the output couplers 109, 110. The output couplers 109, 120 provide corresponding out-coupled beams 135, 134 to a beam combiner 113. The beam combiner 113 provides a combined beam 137 for each guided mode to a phase detector 139. The phase detector 139 generates measurement data by interpreting optical differences in phase between the first and second optical paths, which, respectively, are exposed to the measurement and reference samples 130, 131 for each guided mode, and sends the measurement data to a computer 141 for subsequent analysis.

The integrated optical sensor 105 includes a waveguide 111 that accommodates at least two (2) optical channels or paths 130, 131 on a, e.g., silicon, substrate 202 (see FIG. 2A). Preferably, the substrate 202 is planar; however, the disclosed invention can be practiced with a non-planar substrate without deviating from the scope and spirit of the disclosure. A measurement path 130 extends between an input coupler 108 and an output coupler 110 and a reference path 131 extends between another input coupler 107 and another output coupler 109. A measurement sample 140 is contiguous to the upper surface of the measurement path 130, e.g., approximately midway between the input coupler 108 and output coupler 110. Further, a reference sample 142 is contiguous to the upper surface of the reference path 131, e.g., approximately midway between the input coupler 107 and output coupler 109.

For example, the measurement and reference samples 140, 142 can be liquid or gaseous samples containing amounts of biological or chemical substances of unknown and known concentration, respectively. Target analytes within these liquid or gaseous samples are located on, i.e., bound to, respectively, the upper surfaces of the measurement and reference paths 130, 131 in manners that are well know to those of ordinary skill in the art. Various surface attachment techniques are presented in "Patterning Multiple Antibodies on Polystyrene" by R. A. Brizzolara that was published in *Biosensors and Bioelectronics*, 15, pp. 63–68 (2000), which is incorporated herein by reference. For example, respective upper surfaces of the measurement and/or reference paths 130, 131 can be coated appropriately with known chemically or biologically sensitive layers, and the target analytes within the measurement and/or reference samples 140, 142 then bind to these layers.

Preferably, the measurement and reference paths 130, 131, in association with the input couplers 107, 108 and output couplers 109, 110, provide optical paths for light propagating as gaussian-shaped beams through a thin-film guiding layer, i.e., waveguide 111, of the integrated optical sensor 105. In one embodiment, the measurement path 130 and the reference path 131 are rectilinear sections, each having a length on the order of the length of the integrated optical sensor 105. However, it should be understood that non-rectilinear sections also can be used without deviating from the scope and spirit of this disclosure. Because the guided beams propagating through the measurement and reference paths 130, 131 in the guiding layer are unconfined in the lateral planar dimension, unwanted scattering of the beams within the guiding layer can be minimized, thereby significantly enhancing the sensitivity of the optical sensing platform 100 in comparison to conventional channel-type paths.

It should be noted that the input couplers 107, 108, the output couplers 109, 110, and the optical elements (not shown), e.g., optical fibers, which are used for injecting the beams 132, 133 into the input couplers 107, 108 via the polarization modulator 103, are conventional. Accordingly, specific structures used for implementing these optical elements in the integrated optical sensor 105 are not critical to the present invention, and can take different forms. The laser 102 used as a light source also is conventional and can be implemented as, e.g., a helium-neon (HeNe) laser, a near infrared semiconductor laser, a diode laser or other laser known to those skilled in the art.

In preferred embodiments, the detection and/or measurement of very small numbers of bound targets, including even a single target, from liquid or gaseous samples is accomplished using an interferometric, doubly differential surface detection technique. Preferably, using the above-described optical sensing platform 100, the light source 102, e.g., laser, injects beams 132, 133 into input couplers 107, 108, respectively, via the polarization modulator 103, which enables exciting a plurality of orthogonally polarized spatial modes. Two spatially separated, polarized guided beams propagate unconfined in the lateral planar direction through a first and a second optical path 130, 131 within the guiding layer of the waveguide 111. Each beam 132, 133 preferably propagates through each optical path 130, 131 in each of two orthogonally polarized waveguide modes, and more preferably in the $TE_0$ and $TM_0$ modes, which modes are modulated to propagate independently and sequentially.

As described in greater detail later in this specification, the doubly differential surface detection technique of the present invention then is used to derive a set of first differential measurements, e.g., $\delta n_{TE}$ and $\delta n_{TM}$, for each of the two polarized guided modes propagating sequentially through each of the measurement and reference paths 130, 131, i.e., $$\delta n_{TE} = n_{TE\ measurement} - n_{TE\ reference} \text{ and } \delta n_{TM} = n_{TM\ measurement} - n_{TM\ reference};$$

and a second differential measurement ($\Delta N$) from a combination of the first differential measurements for each guided mode, i.e., $$\Delta N = \delta n_{TE} - \delta n_{TM}.$$

The differential measurements preferably are determined using a programmed microprocessor receiving the data from the fringe detector 304. Such a microprocessor is programmed readily by a normally skilled programmer.

This doubly differential surface detection technique, as implemented on the optical sensing platform 100, provides substantial immunity, i.e., lack of sensitivity, to both inherent thermal and/or mechanical perturbations and external thermal variations in the local index of refraction and also compensates for non-specific binding, thereby advantageously providing the sensitivity and stability required for detecting and/or measuring very small concentrations of substances, e.g., small molecules, bio-molecules, and/or microorganisms, in a measurement sample 140. Indeed, the sensitivity of the disclosed invention can measure even a single bound molecule or pathogen in a measurement sample 140.

As mentioned above, in one embodiment, the measurement path 130 and the reference path 131 can be rectilinear sections. In this embodiment, the rectangular cross sectional dimensions of the optical paths 131, 130, and the wavelength, $\lambda$, of the injected beams 132, 133, are specified so that two orthogonally polarized waveguide modes, i.e., $TE_m$ and $TM_m$, are allowed to propagate sequentially through each path 131, 130. Further, each of the in-coupled, guided beams preferably propagates through the waveguide 11 of the integrated optical sensor 105 as $TE_0$ and $TM_0$ modes.

FIG. 2A shows an embodiment of a cross sectional view of the integrated optical sensor 105 of the present invention, taken along the line 2A—2A. That view shows the measurement and reference paths 130, 131 through the thin film guided wave layer formed on the substrate 202. Further, the measurement sample 140, containing target analytes of unknown concentration, and the reference sample 142, which can contain target analytes of known concentration, are shown contiguous to the upper surfaces of the measurement and reference paths 130, 131, respectively.

Figure 2B:
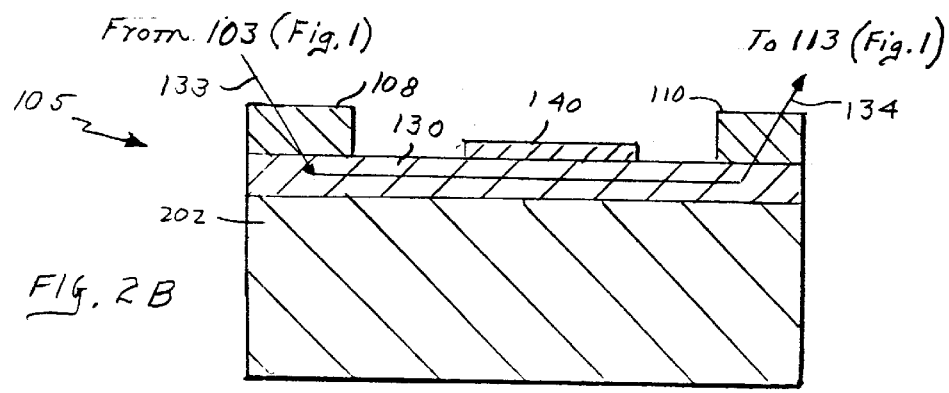
FIG. 2B illustrates a cross sectional view of an embodiment of the integrated optical sensor used with the optical sensing platform of FIG. 1, taken along a line 2B—2B.

FIG. 2B shows an embodiment of a cross sectional view of the integrated optical sensor 105 of the present invention, taken along the line 2B—2B, i.e., for the measurement path 130. It should be noted that the structure described here for the measurement path 130 is identical to the structure for the reference path. That view shows the input coupler 108, the measurement path 130 and sample 140, and the output coupler 110 of the waveguide 111 formed on the substrate 202. The injected beam 133, which comes directly from the polarization modulator 103, can propagate through the input coupler 108 and the measurement path 130. The out-coupled beam 134 propagates through the output coupler 110.

Figure 2C:
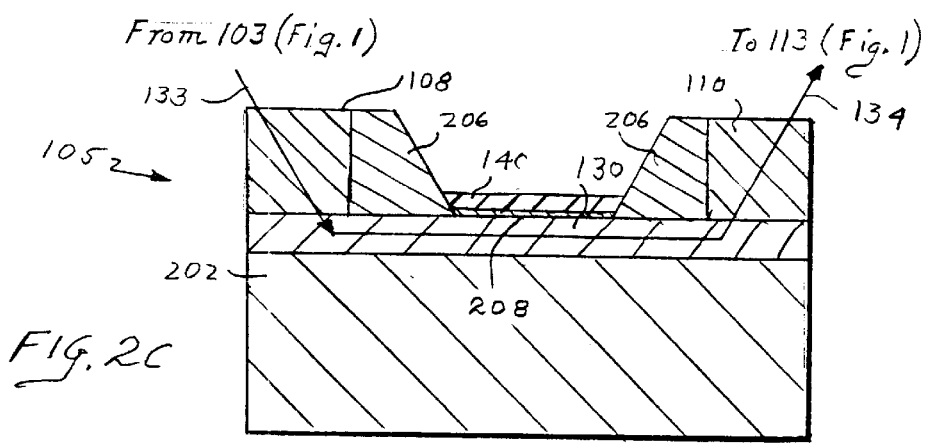
FIG. 2C illustrates a detailed cross sectional view of an embodiment of the integrated optical sensor used with the optical sensing platform of FIG. 1, taken along a line 2C—2C.

FIG. 2C shows a second embodiment of a detailed cross sectional view of the integrated optical sensor 105 taken along the line 2C—2C, i.e., for the measurement path 130. It should be noted that the structure described here for the measurement path 130 is identical to the structure for the reference path. FIG. 2C also shows sidewalls 206 and a well base 208, which are optionally provided on the substrate 202 to produce a well for holding, e.g., a liquid measurement sample 140.

The substrate 202 and the wave guiding layer, including the optical paths 130, 131 of the waveguide 111 can be made of, e.g., glass with a high refractive index, which can be a doped silicon glass, and, more particularly, silicon nitride ($Si_3N_4$). The input couplers 107, 108, the output couplers 109, 110, the sidewalls 206 and the well base 208, can be made of, e.g., silicon dioxide ($SiO_2$).

A waveguide 111 used in optical sensing applications generally has a refractive index (n) that is greater than the refractive index of the substrate 202 on which it is formed, thereby providing a refractive index difference that is large enough to substantially ensure total internal reflection of light propagating through the waveguide 111.

Furthermore, in order to provide the sensitivity and stability required for detecting and/or measuring very small concentrations of substances, e.g., small molecules, biomolecules, and/or microorganisms, in the measurement sample 140, the waveguide 111 of the integrated optical sensor 105 preferably satisfies some additional requirements. For example, the measurement and reference paths 130 and 131 preferably support only the $TE_0$ and $TM_0$ modes, which modes can best detect and/or measure very small concentrations of substances in the measurement sample 140 using the evanescent wave surface detection technique.

The substances in the measurement sample 140 are detected and/or measured by measuring differences in the effective refractive indices ($\delta n$) between the first and second optical paths 130, 131 for both polarized guided modes, $TE_0$ and $TM_0$, i.e., $$\delta n_{TE} = n_{TE\ measurement} - n_{TE\ reference}$$

and $$\delta n_{TM} = n_{TM\ measurement} - n_{TM\ reference},$$

which the polarization modulator 103 causes to propagate sequentially through the measurement and reference paths 130, 131. These differences are proportional to the penetration depths of the evanescent wave fields, corresponding with the $TE_0$ and $TM_0$ modes, into the measurement and reference samples 140, 142, which are contiguous to the measurement and reference paths 130, 131, respectively. Accordingly, the differences in the effective refractive indices of the modes, $\delta n_{TE}$ and $\delta n_{TM}$, are measured with the highest resolution when both of the injected beams 132, 133 propagate through the measurement and reference paths 130, 131 in the $TE_0$ and $TM_0$ modes only.

The wave guiding layer used for propagating light through the integrated optical sensor 105 is preferably as optically uniform as possible. This reduces optical scattering and enhances the sensitivity of the platform 100.

The doubly differential surface detection technique of the present invention, implemented using the optical sensing platform 100, will now be described in detail as follows. Initially, at least one measurement sample 140, is located contiguous to the upper surface of the measurement path 130, e.g., approximately midway between the optical couplers 108, 110 and, a reference sample 142 is located contiguous to the upper surface of the reference path 131, e.g., approximately midway between the optical couplers 107, 109.

As mentioned above, the measurement and reference samples 140, 142 can be liquid or gaseous samples that contain, respectively, known and unknown concentrations of biological or chemical substances. Furthermore, the respective upper surfaces of the measurement and reference paths 130, 131 can be coated with a known chemically or biologically sensitive layer so that the target analytes contained in the measurement and reference samples 140, 142 bind appropriately thereto.

A light source, e.g., laser 102, injects light beams 132, 133 into the polarization modulator 103, which alternately and sequentially sends one of the two orthogonal, polarized modes, i.e., guided or excited modes, to each input coupler 107, 108 of the waveguide 111. The respective modulated, in-coupled, guided beams are excited and propagate through the measurement and reference paths 130, 131. Specifically, the light beams 132, 133 are guided by total internal reflection alternately in the excited $TE_0$ and $TM_0$ modes through the paths 130, 131. As a result, the evanescent wave fields corresponding with the $TE_0$ and $TM_0$ modes, reach out into the substrate 202 and the target analytes within the measurement and reference samples 140, 142 that are bound to the upper surface of the measurement path 130 and reference path 131, respectively.

The guided beams then propagate to the output couplers 109, 110, which provide the corresponding out-coupled beams 135, 134 to the beam combiner 113. The beam combiner 113 combines the beams from each optical path 130, 131, which is to say, that the reference pattern for a $TE_0$ mode is combined with a corresponding measurement pattern for the $TE_0$ mode and a reference pattern for the $TM_0$ mode is combined with a corresponding measurement pattern for the $TM_0$ mode. The combined reference patterns are sent to the phase detector 139 for generating measurement data.

Preferably, the measurement data generated by the phase detector 139 includes optical information relating to relative phase shifts of the $TE_0$ and $TM_0$ excited modes in the out-coupled beams 134, 135. Finally, the phase detector 139 provides the measurement data to a computer 141 for deriving the above-mentioned set of first differential measurements and the second differential measurement.

The set of first differential measurements, i.e., $\delta n_{TE}$ and $\delta n_{TM}$, are obtained, respectively, for each of the two polarized modes, $TE_0$ and $TM_0$, which propagate sequentially through both the measurement and reference paths 130, 131. For example, as the $TE_0$ polarized mode propagates through each optical path 130, 131 of the waveguide 111, evanescent wave fields reach out into the substrate 202 and penetrate the bound samples 140, 142. The difference in the refractive indices of the excited $TE_0$ mode, $$\delta n_{TE} = n_{MEASUREMENT} - n_{REFERENCE},$$

changes as a result of the respective penetration of the evanescent wave fields into the bound target analytes within the measurement and reference samples 140, 142. Likewise, as the $TM_0$ polarized mode propagates through each optical path 130, 131 of the waveguide 111, evanescent wave fields reach out into the substrate 202 and penetrate the bound samples 140, 142. The difference in the refractive indices of the excited $TM_0$ mode, $$\delta n_{TM} = n_{MEASUREMENT} - n_{REFERENCE},$$

also changes as a result of the respective penetration of the evanescent wave fields into the bound target analytes within the measurement and reference samples 140, 142. The set of first differential measurements, i.e., $\delta n_{TE}$ and $\delta n_{TM}$, derived from the two polarized guided modes, $TE_0$ and $TM_0$, propagating through the measurement and reference paths 130, 131, has the effect of subtracting out biochemical instabilities, i.e., noise, resulting from non-specific binding, and also any external thermal dependence of $\delta n_{TE}$ and $\delta n_{TM}$.

These changes in the refractive indices, i.e., $\delta n_{TM}$ and $\delta n_{TE}$, correspond with the above-mentioned set of first differential measurements and are provided by a suitably programmed computer 141, e.g., a microprocessor, using the measurement data provided by the phase detector 139. There are many ways to detect the optical phase change, e.g., by using an array detector spatially matched to an optical interference pattern or by using an unmatched, charge-couple device ("CCD") detector, both of which are well-known to those of ordinary skill in the art. The advantages and disadvantages of these two detectors are reciprocal. Indeed, a CCD detector benefits from having fewer interference pattern alignment problems but requires more difficult data processing. A matched array detector, on the other hand, is more difficult to align, but data processing is simplified.

Very small concentrations of substances, e.g., small molecules, bio-molecules, and/or microorganisms, in the measurement sample 140 can be detected and/or measured by measuring an overall change in the effective refractive indices corresponding to each polarized guided mode, i.e., $\Delta N = \delta n_{TE} - \delta n_{TM}$. This overall change in the effective refractive indices, $\Delta N$, corresponds to the above-mentioned second differential measurement and is proportional to relative difference in the individual phase shifts of the $TE_0$ and $TM_0$ polarized guided modes in the out-coupled beams 134, 135.

Specifically, each polarized light beam propagating sequentially through the measurement and the reference paths 130, 131 outputs one of two orthogonal polarization components, S and P, wherein the S component is generated independently by the $TE_0$ mode and the P component is generated independently by the $TM_0$ mode. The S component is linearly polarized parallel to the plane of the waveguide 111 and the P component is linearly polarized in the direction normal to the plane of the waveguide 111.

The independent measurements of the S and P components have a phase difference, $\delta\Phi(t)$, between them that is dependent upon the relative concentrations of substances, e.g., microorganisms, in the measurement and reference samples 140, 142 located on, i.e., bound to, the upper surfaces of the measurement and the reference paths 130, 131, respectively. Specifically, $\delta\Phi(t)$ is dependent upon the relative penetration depths of the evanescent wave fields corresponding with the $TE_0$ and $TM_0$ modes within the measurement and the reference paths 130, 131 into the measurement and the reference samples 140, 142.

It is known to those of ordinary skill in the art that, for the propagation of light through non-birefringent media, e.g., many of the optical elements described above that make up the optical sensing platform 100, the optical path lengths for the two polarization components, S and P, are substantially equal and, further, that $\delta\Phi(t)$ is not changed during the propagation. This means that, in the absence of target analytes within samples 140, 142 bound to the upper surfaces of the measurement and reference paths 130, 131, the $\delta\Phi(t)$ between the S and P components is the same everywhere in the waveguide 111, even in the presence of inherent thermal and mechanical perturbations. The second differential measurement, i.e., $\Delta N = \delta n_{TE} - \delta n_{TM}$, also relates to the phase difference, $\delta\Phi(t)$, between the S and P components.

As an illustrative example, a measurement sample 140 is provided with a variable concentration of target analytes, which analytes are bound to the surface of the measurement path 130 while a reference sample 142 is provided with a specific concentration of target analytes, which analytes are bound to the surface of the reference path 131. Each of the measurement and reference samples 140, 142 also includes a quantity of non-specific binding elements.

Accordingly, the light beams propagating through the measurement and the reference paths 130, 131 are outputted as beams 134, 135 by the output couplers 110, 109, combined by the beam combiner 113, and the relative phase shifts of the $TE_0$ and $TM_0$ modes in out-coupled beams 134, 135 (due to the penetration of the evanescent wave fields into the target analytes within the measurement and reference samples 140, 142 that are bound to the upper surface of the measurement and reference paths 130, 131) are detected and measured by the phase detector 139, which provides the measurement data to a computer 141 for deriving the above-mentioned set of first differential measurements and the second differential measurement.

Specifically, the set of first differential measurements, i.e., $\delta n_{TE}$ and $\delta n_{TM}$, optically subtracts out the biochemical instabilities and any external thermal dependence; and, the second differential measurement, i.e., $\Delta N = \delta n_{TE} - \delta n_{TM}$, optically subtracts out the inherent instabilities due to temperature changes and mechanical vibrations, which are common to both guided modes. More specifically, the first differential measurement optically subtracts out the biochemical instabilities resulting from the non-specific binding, thereby measuring only the concentration of target analytes in the measurement sample 140 relative to the concentration of target analytes, if any, in reference sample 142. Thus, immunity, i.e., lack of sensitivity, to environmental effects, such as temperature changes and mechanical vibrations, and biochemical effects, such as non-specific binding, advantageously makes the optical sensing platform 100 of the present invention highly stable with a significantly higher system SNR than conventional systems. Indeed, preferred embodiments of the present invention can produce a degree of accuracy that is at least about an order of magnitude greater than devices of the prior art.

Moreover, the propagation modulator 103 effectively filters out low frequency, e.g., less than about 1000 Hertz, perturbations from noise sources, thereby significantly increasing the system signal-to-noise ratio (SNR).

Figure 3:
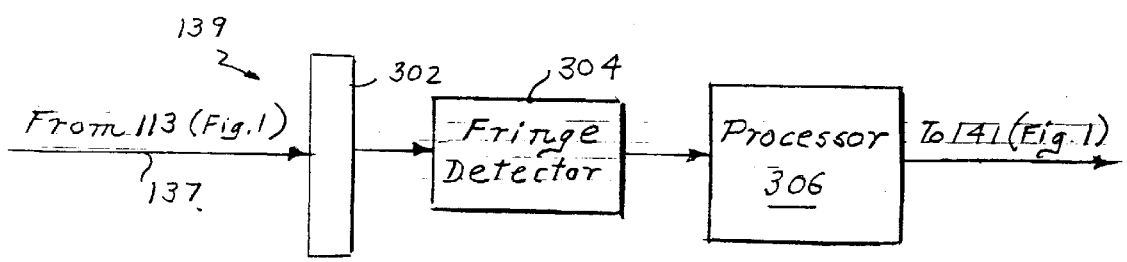
FIG. 3 illustrates a block diagram of an embodiment of the phase detector used with the optical sensing platform of FIG. 1.

FIG. 3 shows a detailed view of an embodiment of the phase detector 139, which preferably includes a fringe imaging lens 302, a fringe detector 304, and a processor 306 that produces a phase value in digital format and provides the value to the computer 141 for data logging and/or subsequent processing.

Preferably, the beam combiner 113 combines the out-coupled beams 134, 135, producing a combined beam 137, from which produces an optical interference pattern, commonly known as a fringe or a spatial heterodyne pattern, which generally includes a series of uniform, sinusoidally distributed, light and dark areas. The fringe-imaging lens 302 focuses the optical interference pattern onto the fringe detector 304, which is, e.g., a matched photodiode array detector or an unmatched CCD detector. Because the integrated optical sensor 105 preferably supports the $TE_0$ and $TM_0$ modes at $\lambda$ equal to about 0.4 to 1.0 $\mu m$, the matched photodiode array can be suitably implemented as a silicon array.

Next, the fringe detector 304 selectively samples the optical interference pattern to detect any translational shifts in fringe positions relative to the overall interference pattern. These translational shifts are proportional to changes in the relative phase, $\delta\Phi(t)$. As described above, these phase shifts, are caused by and are proportional to the penetration of the evanescent wave fields into the concentration of bound analytes within the measurement and reference samples 140, 142.

For example, the optical phase detector 304 can be constructed using a linear array of photodetectors. In one method, e.g., a spatial heterodyne fringe pattern is focused onto the detector array without regard to the number of pixels sampling a complete fringe. Each detector pixel is sampled and the respective signals are processed. The processing typically consists of calculating the amplitude and conjugate phase for each spatial frequency of the sampled imaged interference pattern. In a preferred embodiment, this can be accomplished by calculating the Fourier transform of the array of sampled light intensities, identifying the frequency of the fringe pattern, and recording its corresponding phase value, $\Phi$. This recorded phase value is equal to the optical phase, $\Phi$, of the interferometer.

Figure 5A:
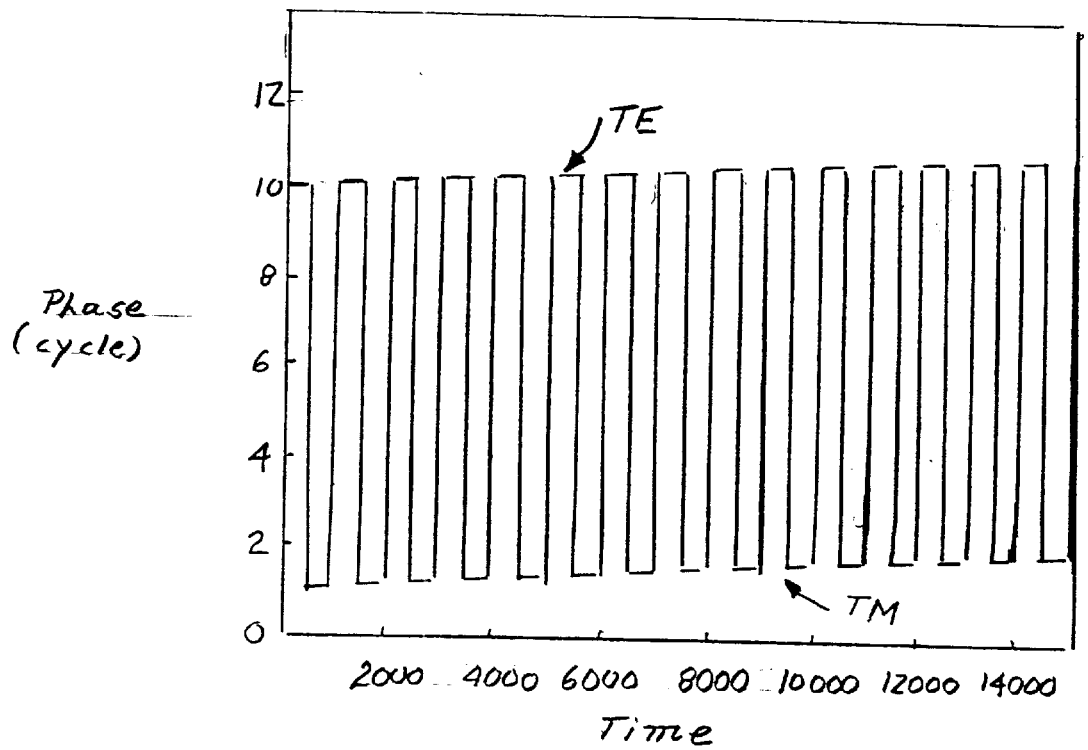
FIGS. 5(A and B) show an embodiment of modulated time-phase data.
Figure 5B:
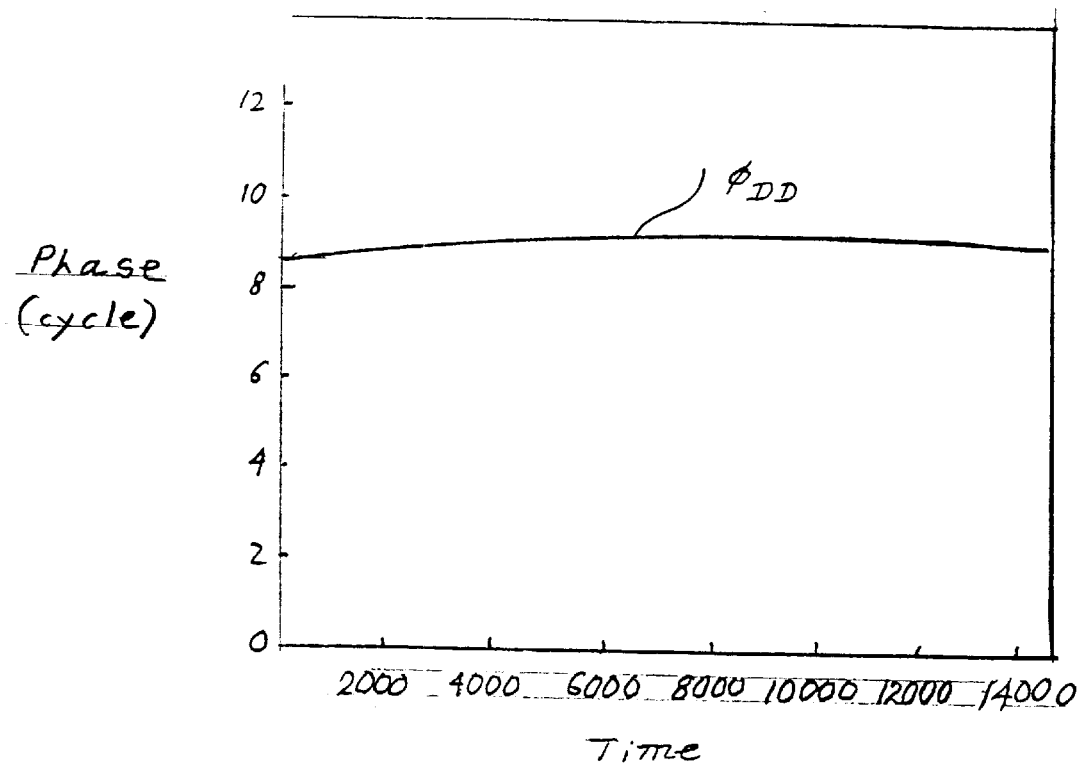

FIG. 5a shows an exemplary graph, which is shown as phase (in cycles) versus time, of typical results from the first set of differential measurements. Indeed, FIG. 5a shows the amplitude and conjugate phase for each spatial frequency, i.e., TE and TM, of the sampled imaged interference pattern. FIG. 5b shows, further, an exemplary graph of a typical phase-time relationship using doubly differentiated results.

In a second method, the frequency of the interference pattern is carefully matched with the spacing of the detector pixels. The intensity (I) sampled by a pixel is given by $$I(x) = I_{DC} + I_{AC} \cos(\Phi + \Delta N)$$

where $\Phi$ is the optical phase and $\Delta N$ is the position of the sampled pixel with respect to spatial frequency of the interference pattern.

In one embodiment, one complete fringe can be sampled by four detector pixels as describe by Helmers et al., Applied Optics, 35(4), p 676, 1996, which is incorporated herein by reference. Here $\Delta N$ is equal to $0$, $\pi/2$, $\pi$, and $3\pi/2$. In another embodiment, one complete fringe can be sampled by three detector pixels as described by U.S. Pat. No. 5,530,543 to Hercher, here $\Delta N$ is equal to $2\pi/3$, $0$, and $-2\pi/3$. A distinct advantage of the first method is nominal constraints on alignment compared to the second method. In contrast, the corresponding processing requirements are significantly greater compared with the second method.

The preferred phase detector 139 has the capability of recovering relative phase information, $\delta\Phi(t)$, at a level of precision equal to about $10^{-7}$ cycles/$\sqrt{Hz}$. This is an important advantage for the detection and/or measurement of small molecules, bio-molecules, and/or microorganisms because it provides the high sensitivity necessary for rapidly and directly detecting, e.g., a single bound target analyte, which is typically a very time consuming task using conventional detection techniques, and for the discrimination or binding of small molecules to significantly larger complexes. The preferred optical sensing platform 100 of the present invention therefore has both the sensitivity and speed required for directly detecting and/or measuring substances such as small molecules, bio-molecules and/or microorganisms in real time applications.

It can be appreciated that numerous alternative embodiments or variations can be made. For example, it was described that the optical sensing platform 100 of the present invention includes an integrated optical sensor 105 with a measurement path 130 and a reference path 131. However, this was merely an illustrative example, and other configurations are available. For example, the optical sensing platform 100 alternatively can be configured as a Mach-Zehnder interferometer, an embodiment of which is disclosed in, e.g., U.S. Pat. No. 4,515,430 to Johnson.

A Mach-Zehnder interferometer includes structure for bifurcating a light beam into two separate and distinct optical paths, and then combining the two light beams. Hence, a Mach-Zehnder-type interferometer configuration can be used for performing the double differential measurements required by the present invention.

Channel-type waveguides, which are well known to those of ordinary skill in the art, also can be used. However, it should be understood that because the guided beams propagating through the optical paths of some prior art channel-type waveguides are not unconfined in the lateral dimension as in a preferred embodiment of the integrated optical sensor 105 shown in FIG. 1, the scattering of the light beams within the guiding layer is not optimally minimized. Therefore, channel-type waveguides may not provide the optimal level of sensitivity for measuring very small numbers of targets in the measurement sample 140.

It was described that suitable optical fibers can be used for injecting the light beams 132, 133 into the propagation modulator 103 and/or as a waveguide. However, this was also merely an illustrative example. The respective light beams alternatively can be injected into the propagation modulator 103 via propagation in free-space. Similarly, the out-coupled light beams 134, 135 can be provided to the beam combiner 113 via propagation in free-space.

It was described that the analytes in the measurement and reference samples 140, 142 can be bound to the upper surfaces of the measurement and reference paths 130, 131 using a chemically or biologically sensitive layer. It was also described that wells can be formed in the surface of the integrated optical sensor 105 for holding the measurement and reference samples 140, 142. However, these were merely illustrative examples. Specifically, because the optical sensing platform 100 of the present invention is particularly useful for detecting and/or measuring target analytes in a measurement sample 140, a plurality of highly specific probes alternatively can be immobilized on the surface of the measurement path 130.

For example, certain compatible probes, e.g., antibody or nucleic acid probes, can be used for binding variable concentrations of small molecules, bio-molecules or microorganisms in the measurement sample 140 to the upper surface of the measurement path 130. Further, the probes can be attached to the upper surface of the measurement path 130, e.g., either covalently or by using an intermediate linker.

Similarly, suitable probes can be used for binding specific concentrations of, e.g., small molecules, bio-molecules, and/or microorganisms to the upper surface of the reference path 131. In this way, the reference path 131 advantageously serves as both a biochemical and an environmental reference, thereby subtracting out interfering biological and/or chemical binding and removing extraneous temperature effects.

It was described that the optical sensing platform 100 of the present invention includes an integrated optical sensor 105. However, this was also merely an illustrative example. The optical sensing platform 100 alternatively can be implemented using a plurality of separate waveguides 111. Further, it was described that the waveguide 111 used with the optical sensing platform 100 includes one measurement path 130 and one reference path 131. However, this was merely an illustrative example. The optical sensing platform 100 of the present invention alternatively can be implemented with more than one measurement path 130 and/or more than one reference path 131, depending upon the requirements of the optical sensing application.

The present invention has been described in detail including the preferred embodiments thereof. However, it should be appreciated that those skilled in the art, upon consideration of the present disclosure, may make modifications and/or improvements of this invention that are within the scope and spirit of this invention as set forth in the following claims.

What is claimed is:

1. An optical sensing platform for detecting and/or measuring the amount of a substance in a sample using an interferometric surface detection technique, the platform comprising:
   at least one pair of optical channels, comprising:
      a first optical channel having an upper measurement surface for contact with the sample, and
      a second optical channel having an upper surface for contact with a reference sample;
   a light source for introducing optical beams into the at least one pair of optical channels;
   a light modulator; and a phase detector for detecting optical phase differences between the respective optical beams from the at least one pair of first and second optical channels;
wherein the light modulator comprises a polarization modulator.

2. The optical sensing platform as recited in claim 1, wherein the polarization modulator is selected from the group consisting of a ferro-electric liquid crystal, a pockel cell, and a photoelastic modulator.

3. The optical sensing platform as recited in claim 1, wherein the polarization modulator enables the excitation of at least two unique guided modes of the respective optical beams to propagate independently and sequentially through the at least one pair of optical channels.

4. The optical sensing platform as recited in claim 3, wherein the at least two unique guided modes of the respective optical beams propagating independently and sequentially through the at least one pair of optical channels comprise a transverse electric and a transverse magnetic excited mode.

5. The optical sensing platform as recited in claim 1, wherein the substance is bound to a coating provided on the upper measurement surface.

6. The optical sensing platform as recited in claim 5, wherein the substance is bound to the upper measurement surface using antibody probes.

7. The optical sensing platform as recited in claim 1, wherein at least one pair of optical channels is formed on a common waveguide.

8. The optical sensing platform as recited in claim 7, wherein the common waveguide is substantially planar.

9. The optical sensing platform as recited in claim 7, wherein the optical beams propagate through the at least one pair of optical channels of the waveguide as gaussian light beams substantially unconfined in the lateral direction.

10. The optical sensing platform as recited in claim 1, wherein the substance is selected from a group consisting of microorganisms, small molecules, and bio-molecules.

11. The optical sensing platform as recited in claim 1, wherein the phase detector comprises a fringe imaging lens and a fringe detector, wherein the fringe imaging lens focuses a plurality of optical fringe patterns for a plurality of guided modes on the fringe detector from which a plurality of phase differences in refractive indices can be measured.

12. The optical sensing platform as recited in claim 1, wherein the phase detector is selected from the group consisting of a matched, multi-element phase array detector and an unmatched, charge-couple device detector.

13. The optical sensing platform as recited in claim 1, wherein the detected optical phase differences comprise a plurality of first differential measurements and at least one second differential measurement for each pair of optical channels.

14. The optical sensing platform as recited in claim 13, wherein the detected optical phase differences in the plurality of first differential measurements are proportional to changes in the effective refractive indices ($\delta n$) between the at least one measurement sample and the at least one reference sample for a transverse electric mode, $\delta n_{TE} = n_{TE\ measurement} - n_{TE\ reference}$, and for a transverse magnetic mode, $\delta n_{TM} = n_{TM\ measurement} - n_{TM\ reference}$.

15. The optical sensing platform as recited in claim 14, wherein the detected optical phase difference in the effective refractive indices further comprises a second differential measurement between $TE_0$ and $TM_0$ excited modes, i.e., $\Delta N = \delta n_{TE} - \delta n_{TM}$.

16. The optical sensing platform as recited in claim 1, further comprising:

a beam combiner to combine a plurality of respective optical beams coupled out of the at least one pair of first and second optical channels and provide the combined beams to the phase detector, and
a computer to perform necessary mathematical operations and to store the results thereof, having software and database memory therefor.

17. A method for detecting and/or measuring the quantity of a substance in at least one measurement sample, the method comprising the steps of:

providing a device as set forth in claim 1;
locating the at least one measurement sample, having a refractive index ($n_{MEASUREMENT}$), and the at least one reference sample, having a refractive index ($n_{REFERENCE}$), respectively, contiguous to an upper surface of at least one first optical channel and at least one second optical channel;
introducing an optical beam from a light source into a light modulator, wherein the light modulator enables exciting a plurality of orthogonally polarized guided modes, which guided modes propagate sequentially in the at least one first optical channel and the at least one second optical channel;
detecting a plurality of optical phase differences as a function of time using a phase detector, wherein the plurality of optical phase differences are produced by the plurality of orthogonally polarized guided modes; and
performing at least one set of doubly differentiating measurements using the plurality of optical phase differences between the at least one measurement sample and the at least one reference sample.

18. The method as recited in claim 17 wherein the introducing step further comprises exciting the optical beam so that the plurality of orthogonally polarized guided modes comprises at least one transverse electric (TE) guided mode and at least one transverse magnetic (TM) guided mode.

19. The method as recited in claim 18, wherein detecting a plurality of optical phase differences comprises:

detecting an optical phase difference in refractive indices between the at least one measurement sample and the at least one reference sample for a transverse electric guided mode, and
detecting an optical phase difference in refractive indices between the at least one measurement and the at least one reference samples for a transverse magnetic, guided mode.

20. The method as recited in claim 17, wherein the substance is selected from a group consisting of microorganisms, small molecules, and bio-molecules.

21. The method as recited in claim 17, wherein the step of performing at least one set of doubly differentiating measurements further comprises:

performing a set of first differential measurements, wherein the set of first differential measurements comprises detecting and/or measuring a plurality of phase differences for a transverse electric and a transverse magnetic excited modes; and
performing a second differential measurement, wherein the second differential measurement comprises an overall difference between the phase differences detected for the transverse electric and the transverse magnetic guided modes in the respective first differential measurements.

22. The method as recited in claim 21, wherein the set of first differential measurement phase differences are proportional to changes in the respective effective refractive indices between said first and second optical channels, i.e., $$\delta n_{TE} = n_{TE\ measurement} - n_{TE\ reference} \text{ and } \delta n_{TM} = n_{TM\ measurement} - n_{TM\ reference}.$$

23. The method as recited in claim 21, wherein the second differential measurement overall difference between the optical phase differences is proportional to the difference between the respective effective refractive indices of the transverse electric and transverse magnetic guided modes, i.e., $\Delta N = \delta n_{TE} - \delta n_{TM}$.

24. The method as recited in claim 23, wherein determining the overall difference between the phase differences of the transverse electric guided mode with respect to the transverse magnetic guided modes comprises the substeps of:
- selectively sampling an optical fringe pattern derived from the refractive index of a measurement sample and an optical fringe pattern derived from the refractive index of a reference sample for the transverse electric guided mode and the transverse magnetic guided mode;
- detecting shifts in fringe positions of the phase of the measurement sample relative to that of the reference sample for the transverse electric guided mode and the transverse magnetic guided mode using a phase detector; and
- subtracting the phase difference of the transverse electric guided mode from the phase difference of to the transverse magnetic guided mode.

25. The method as recited in claim 21, wherein detecting the plurality of optical phase differences between the phase differences of the reference with respect to the measurement sample for the transverse electric and transverse magnetic guided modes comprises the substeps of:
- selectively sampling a pair of optical fringe patterns comprising an optical fringe pattern of the refractive index of a measurement sample and an optical fringe pattern of the refractive index of a reference sample measured at the same time, and
- detecting shifts in the optical fringe pattern of the measurement sample relative to the sampled fringe pattern of the reference sample using a fringe detector.

26. An optical sensing platform for detecting and/or measuring the amount of a substance in a sample using an interferometric surface detection technique, the platform comprising:
- at least one pair of optical channels, comprising:
  - a first optical channel having an upper measurement surface for contact with the sample, and
  - a second optical channel having an upper surface for contact with a reference sample;
- a light source for introducing optical beams into the at least one pair of optical channels;
- a light modulator comprising a device that enables exciting at least two unique guided modes in the at least one pair of optical channels; and
- a phase detector for detecting optical phase differences between the respective optical beams from the at least one pair of first and second optical channels, wherein said at least two unique guided modes are excited independently and sequentially.

27. The optical sensing platform as recited in claim 26, wherein the substance is bound to a coating provided on the upper measurement surface.

28. The optical sensing platform as recited in claim 27, wherein the substance is bound to the upper measurement surface using antibody probes.

29. The optical sensing platform as recited in claim 26, wherein at least one pair of optical channels is formed on a common waveguide.

30. The optical sensing platform as recited in claim 29, wherein the common waveguide is substantially planar.

31. The optical sensing platform as recited in claim 29, wherein the optical beams propagate through the at least one pair of optical channels of the waveguide as gaussian light beams substantially unconfined in the lateral direction.

32. The optical sensing platform as recited in claim 26, wherein the substance is selected from a group consisting of microorganisms, small molecules, and bio-molecules.

33. The optical sensing platform as recited in claim 26, wherein the phase detector comprises a fringe imaging lens and a fringe detector, wherein the fringe imaging lens focuses a plurality of optical fringe patterns for a plurality of guided modes on the fringe detector from which a plurality of phase differences in refractive indices can be measured.

34. The optical sensing platform as recited in claim 26, wherein the phase detector is selected from the group consisting of a matched, multi-element phase array detector and an unmatched, charge-couple device detector.

35. The optical sensing platform as recited in claim 26, wherein the detected optical phase differences comprise a plurality of first differential measurements and at least one second differential measurement for each pair of optical channels.

36. The optical sensing platform as recited in claim 35, wherein the detected optical phase differences in the plurality of first differential measurements are proportional to changes in the effective refractive indices ($\delta n$) between the at least one measurement sample and the at least one reference sample for a transverse electric mode, $\delta n_{TE} = n_{TE\ measurement} - n_{TE\ reference}$, and for a transverse magnetic mode, $\delta n_{TM} = n_{TM\ measurement} - n_{TM\ reference}$.

37. The optical sensing platform as recited in claim 36, wherein the detected optical phase difference in the effective refractive indices further comprises a second differential measurement between $TE_0$ and $TM_0$ excited modes, i.e., $\Delta N = \delta n_{TE} - \delta n_{TM}$.

38. The optical sensing platform as recited in claim 26, further comprising:
- a beam combiner to combine a plurality of respective optical beams coupled out of the at least one pair of first and second optical channels and provide the combined beams to the phase detector, and
- a computer to perform necessary mathematical operations and to store the results thereof, having software and database memory therefor.

* * * * *